US008101656B2

(12) United States Patent
Fischer et al.

(10) Patent No.: US 8,101,656 B2
(45) Date of Patent: Jan. 24, 2012

(54) USE OF 2,2-DIMETHYL-3-(2,4-DICHLOROPHENYL)-2-OXO-1-OXASPIRO[4,5]DEC-3-EN-4-YL BUTANOATE FOR CONTROLLING ACARIDES

(75) Inventors: Reiner Fischer, Monheim (DE); Ernst Brück, Bergisch Gladbach (DE)

(73) Assignee: Bayer CropScience AG, Monheim (DE)

( * ) Notice: Subject to any disclaimer, the term of this patent is extended or adjusted under 35 U.S.C. 154(b) by 1244 days.

(21) Appl. No.: 10/563,803

(22) PCT Filed: Jul. 2, 2004

(86) PCT No.: PCT/EP2004/007225
§ 371 (c)(1),
(2), (4) Date: Jun. 28, 2006

(87) PCT Pub. No.: WO2005/004605
PCT Pub. Date: Jan. 20, 2005

(65) Prior Publication Data
US 2007/0015825 A1    Jan. 18, 2007

(30) Foreign Application Priority Data
Jul. 14, 2003   (DE) .................. 103 31 674

(51) Int. Cl.
*A01N 43/02* (2006.01)
*A01N 43/12* (2006.01)
*A01N 25/00* (2006.01)
(52) U.S. Cl. ................... 514/462; 514/449; 424/405
(58) Field of Classification Search .................. 514/449, 514/462; 424/405
See application file for complete search history.

(56) References Cited

U.S. PATENT DOCUMENTS
5,262,383 A * 11/1993 Fischer et al. ................. 504/195
5,380,732 A * 1/1995 Blade ............................ 514/351

FOREIGN PATENT DOCUMENTS
EP   0 528 156 A1   2/1993
WO  WO 01/68625 A1  9/2001

OTHER PUBLICATIONS

Wachendorff et al., BAJ 2740, a novel broad spectrum acaricide, Proceedings of the Brighton Crop Protection Conference-Pests and Diseases, pp. 53-58, 2000.*
Elbert et al., Worldwide uses of the new acaricide Envidor® in perennial crops, Pflanzenschutz-Nachrichten Bayer, 55, 2002, 287-304.*
Callender, Chemistry of grapes and other fruits as the raw materials involved in winemaking, Advances in Chemistry, vol. 137, pp. 11-49, 1974.*
Weidhaas, Spider Mite and Other Acarina on Trees and Shrubs, Journal of Arboriculture, 5(1): Jan. 1979, pp. 9-15.*
Wikipedia article, entitled, "Berry"—accessed on Feb. 6, 2011 at http://en.wikipedia.org/wiki/Berry.*
"Online article, entitled, Invasive Mite Identification"—accessed on Feb. 6, 2011 at keys.lucidcentral.org/keys/v3/mites/Invasive_Mite_Identification/key/Tetranychinae/Media/Html/Oligonychus.htm.*
Online definition of "family Tetranychidae"—accessed on Feb. 6, 2011 at www.thefreedictionary.com/family+Tetranychidae.*
West, K., et al., "Spruce Spider Mite Biology and Control in Christmas Trees," Oregon State University Extension Service, Special Report 875, United States (1991) (XP007914044).
Yigit, A. & Erkilic, L., "Studies on the chemical control of *Tetranychus cinnabarinus* Boisd. (Acarina:Tetranychidae), a pest of strawberry in the East Mediterranean region of Turkey," *Crop Protection* 11:433-438, Butterworth-Heinemann Ltd., United Kingdom (1992) (XP002592747).
Elbert, A., et al., "Worldwide uses of the new acaricide Envidor® in perennial crops," *Pflanzenschutz-Nachrichlen Bayer* 55:287-304, (2002).
Fischer, R., et al., "chemistry and stereochemistry of spirodiclofen (BAJ 2740)," *Pflanzenschutz-Nachrichten Bayer* 55:137-148, (2002).
International Search Report for International Patent Application No. PCT/EP2004/007225, European Patent Office, Rijswijk, NL, mailed Oct. 11, 2004.
Dialog File 351, Accession No. 10959201, WPI English language abstract for WO 01/68625 Accessed Jul. 25, 2006.

* cited by examiner

*Primary Examiner* — James H. Alstrum-Acevedo
(74) *Attorney, Agent, or Firm* — Sterne, Kessler, Goldstein & Fox P.L.L.C.

(57) ABSTRACT

The present invention relates to the use of 2,2-dimethyl-3-(2, 4-dichlorophenyl)-2-oxo-1-oxaspiro[4.5]dec-3-en-4-yl butanoate for controlling acarids in hops, kiwi fruit, soft fruit, nuts, coffee, tropical fruit, spices and conifers.

3 Claims, No Drawings

USE OF 2,2-DIMETHYL-3-(2,4-DICHLOROPHENYL)-2-OXO-1-OXASPIRO[4,5]DEC-3-EN-4-YL BUTANOATE FOR CONTROLLING ACARIDES

The present invention relates to the use of 2,2-dimethyl-3-(2,4-dichlorophenyl)-2-oxo-1-oxaspiro[4.5]dec-3-en-yl butanoate for controlling acarids in hops, kiwi fruit, soft fruit, nuts, coffee, tropical fruit, spices and conifers.

The compound 2,2-dimethyl-3-(2,4-dichlorophenyl)-2-oxo-1-oxaspiro[4.5]dec-3-en-yl butanoate is known from EP-A-528 156.

The acaricidal activity of 2,2-dimethyl-3-(2,4-dichlorophenyl)-2-oxo-1-oxaspiro[4.5]dec-3-en-yl butanoate is also known from EP-A-528 156.

Surprisingly, it has now been found that 2,2-dimethyl-3-(2,4-dichlorophenyl)-2-oxo-1-oxaspiro[4.5]dec-3-en-yl butanoate is particularly suitable for controlling acarids in hops, kiwi fruit, soft fruit, nuts, coffee, tropical fruit, spices and conifers.

Accordingly, the present invention relates to the use of 2,2-dimethyl-3-(2,4-dichlorophenyl)-2-oxo-1-oxaspiro[4.5]dec-3-en-yl butanoate for controlling acarids in hops, kiwi fruit, soft fruit, nuts, coffee, tropical fruit, spices and conifers.

2,2-Dimethyl-3-(2,4-dichlorophenyl)-2-oxo-1-oxaspiro[4.5]dec-3-en-yl butanoate has the following formula (I):

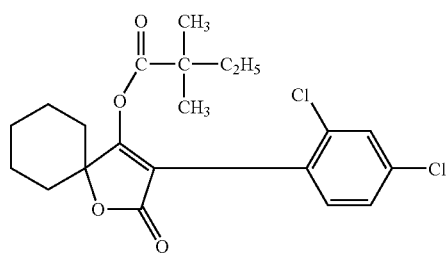

The preparation of the compound of the formula (I) is described in EP-A-1 272 480.

The compound of the formula (I) can preferably be used for controlling arthropods from the class of the *Arachnida*, for example *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp. It is especially preferred to control *Panonychus* spp. and *Tetranychus* spp.

The compound of the formula (I) can preferably be employed in hops; kiwi fruit; soft fruit such as, for example, currant, gooseberry, raspberry, blackberry, strawberry, blueberry; nuts such as, for example, almonds, pistachios, beech, cashew nuts, hazelnuts, brazil nuts, butter nuts, chestnut, hickory nuts, macadamia nuts, pecan nuts, coconuts, walnuts; tropical fruits such as, for example, mango, papaya, dates; coffee and spices such as, for example, chilli; and conifers such as, for example, spruces and firs.

These plants can be obtained by traditional breeding and optimization methods or else by biotechnological methods and genetic engineering methods or combinations of these methods, including the transgenic plants and including the plant varieties which are capable or not capable of being protected by Plant Breeders' Rights. Plant parts are understood as meaning all aerial and subterraneous parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation materials, for example cuttings, tubers, rhizomes, slips and seeds.

The inventive treatment of the plants and plant parts with the active ingredients is carried out directly or by acting on their environment, habitat or store, using the customary treatment methods, for example by dipping, spraying, atomizing, misting, scattering, painting on and, in the case of propagation material, in particular seeds, furthermore by coating with one or more coats.

The active ingredient of the compound of the formula (I) can be converted into the customary formulations, such as solutions, emulsions, wettable powders, suspensions, powders, dusts, pastes, soluble powders, granules, suspoemulsion concentrates, natural and synthetic materials impregnated with active ingredient, and ultrafine encapsulations in polymeric substances.

These formulations are produced in a known manner, for example by mixing the active ingredients with extenders, i.e. liquid solvents and/or solid carriers, if appropriate using surface-active agents, i.e. emulsifiers and/or dispersants and/or foam-forming agents.

If water is used as extender, it is also possible to use for example organic solvents as cosolvents. Liquid solvents which are suitable are essentially: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and water.

Solid carriers which are suitable are:

for example ammonium salts and ground natural minerals such as kaolins, clays, talc, chalk, quartz, attapulgite, montmorillonite or diatomaceous earth and ground synthetic minerals such as highly disperse silica, alumina and silicates; solid carriers which are suitable for granules are: for example crushed and fractionated natural rocks such as calcite, marble, pumice, sepiolite, dolomite, and synthetic granules of inorganic and organic meals, and granules of organic material such as sawdust, coconut shells, maize cobs and tobacco stalks; suitable emulsifiers and/or foam-forming agents are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates and protein hydrolyzates; suitable dispersants are: for example lignin-sulfite waste liquors and methylcellulose.

Adhesives such as carboxymethylcellulose, natural and synthetic polymers in the form of powders, granules or latices such as gum arabic, polyvinylalcohol, polyvinyl acetate, and natural phospholipids such as cephalins and lecithins and synthetic phospholipids may be used in the formulations. Further additives can be mineral and vegetable oils.

Colors such as inorganic pigments, for example iron oxide, titanium oxide, Prussian Blue, and organic dyestuffs, such as alizarin, azo and metal phthalocyanin dyestuffs and micronutrients such as salts of iron, manganese, boron, copper, cobalt, molybdenum and zinc can be used.

In general, the formulations comprise between 0.1 and 95% by weight of active ingredient, preferably between 0.5 and 90%.

The active ingredient content of the use forms prepared from the commercially available formulations can vary within wide ranges. The active ingredient concentration of the use forms can be from 0.0000001 up to 95% by weight of active ingredient, preferably between 0.0001 and 1% by weight.

They are applied in a customary manner which is adapted to suit the use forms.

USE EXAMPLES

Example A

Pest: *Tetranychus Urticae*
Crop: Hops

The compound of the formula (I) (240SC) was tested at a concentration of 0.0048% a.i. in comparison with cis-cyhalothrin (050EC) at 0.005% a.i. The compound of the formula (I) was used at an early stage of the infestation of the pest, while cis-cyhalothrin was applied when the infestation had progressed to a high level.

The spray mixture (2000 l/ha) was applied using a knapsack sprayer operated with compressed air.

The plot size was 6 plants, the number of replications per test variant was 2.

The activity against spider mites was determined 4, 14 and 21 days (compound of the formula (I)) and 4, 11 and 18 days (cis-cyhalothrin) after the treatment by counting the live animals/leaf (10 leaves/plot) and calculating the efficacy using Abbott's formula.

TABLE A

| | Tetranychus urticae/Hops | | | | | |
|---|---|---|---|---|---|---|
| | Concentration | Efficacy in % Abbott | | | | |
| Active ingredients | % a.i./ha | 4* | 11* | 14* | 18* | 21* |
| Compound of the formula (I) (240 SC) | 0.0048 | 90 | | 94 | | 93 |
| Cis-cyhalothrin (050 EC) | 0.005 | 59 | 57 | | 0 | |

*Days after treatment

Example B

Pest: *Tetranycus Urticae*
Crop: Hops

The compound of the formula (I) (240SC) was tested at a concentration of 0.0144% a.i. in comparison with the standard Amitraz (200 EC) at 0.05% a.i. The mixture was sprayed once.

The spray mixture (2200 l/ha) was applied using a trailed machine operated by a tractor. The plot size was 60 plants, and 2 replications were carried out per test variant.

The activity against spider mites was determined 5, 12, 19 and 34 days after the treatment by counting the live animals/leaf (60 leaves/plot) and calculating the efficacy using Abbott's formula.

TABLE B

| | Tetranychus urticae/Hops | | | |
|---|---|---|---|---|
| | | Efficacy in % Abbott | | |
| Active ingredients | Concentration % a.i./ha | 5* | 12* | 19* |
| Compound of the formula (I) (240 SC) | 0.0144 | 89.7 | 98.1 | 99.6 |
| Amitraz (200 EC) | 0.05 | 80.1 | 96.3 | 92.2 |

*Days after treatment

Example C

Pest: *Tetranychus Urticae*
Plant: Black Walnut Tree

The compound of the formula (I) (240 SC) was tested at a concentration of 2.02 ounces a.i. per 100 gallons (=0.126 pounds a.i. per acre) in comparison with PYRAMAT (Pyridaben, 75 WP) at an application rate of 0.125 pound a.i. per acre.

The spray mixture (100 gallons per acre) was applied by means of a motor-operated hand-held sprayer.

The test was carried out with one tree per plot and three replication experiments.

The efficacy against spider mites was calculated by counting the live eggs and nymphs on eight leaves per tree before and one, two and six weeks after the application and subsequently calculated using the formula of Henderson & Tilton.

| Compound | Application rate in pounds of a.i. per acre | Efficacy in Henderson&Tilton % against EGGS | | |
|---|---|---|---|---|
| | | 1 WAA | 2 WAA | 6 WAA |
| Compound of the formula (I) (240 SC) | 0.126 | 100 | 100 | 64 |
| PYRAMITE (75 WP) | 0.125 | 93 | 73 | 0 |

| Compound | Application rate in pounds of a.i. per acre | Efficacy in Henderson&Tilton % against NYMPHS | | |
|---|---|---|---|---|
| | | 1 WAA | 2 WAA | 6 WAA |
| Compound of the formula (I) (240 SC) | 0.126 | 100 | 100 | 83 |
| PYRAMITE (75 WP) | 0.125 | 99 | 94 | 79 |

Example D

Pest: *Eotetranychus Hicoriae*
Plant: Pecan nut tree

The compound of the formula (I) (240 SC) was tested at an application rate of 0.313 lb a.i. per acre in comparison with ACRAMIT (Bifenazate, 50 WP) at 0.50 pound of a.i. per acre.

The spray mixture (105 gallons per acre) was applied by means of a motor-operated hand-held sprayer.

The experiment was carried out with one tree per plot and four replication experiments.

The efficacy against the pecan leaf scorch mite was determined by counting the number of live mites on five leaves per tree 6 and 13 days after the application and subsequently calculated by means of the Abbott formula.

| Compound | Application rate in pounds a.i. per acre | Efficacy in Abbot % | |
|---|---|---|---|
| | | 6 DAA | 13 DAA |
| Compound of the formula (I) (240 SC) | 0.313 | 100 | 80 |
| ACRAMITE (50 WP) | 0.5 | 86 | 20 |

What is claimed is:

1. A method for controlling acarids, comprising contacting a compound of the formula (I)

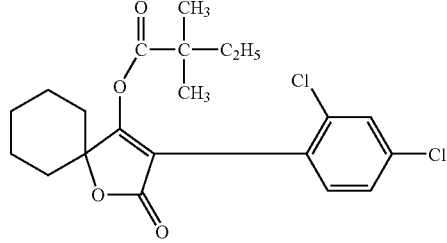

(I)

with hops, soft fruit selected from the group consisting of currant, gooseberry, raspberry, blackberry, strawberry and blueberry, or conifers, wherein the conifers are selected from the group consisting of spruces and firs, and wherein the compound of formula (I) is applied at a concentration of 0.0048% active ingredient per hectare to 0.0144% active ingredient per hectare.

2. The method of claim 1 for controlling acarids in soft fruit selected from the group consisting of currant, gooseberry, raspberry, blackberry, strawberry and blueberry.

3. The method of claim 1 for controlling acarids in spruces or firs, wherein the compound of formula (I) is applied at a concentration of 0.0048% active ingredient per hectare to 0.0144% active ingredient per hectare.

* * * * *